United States Patent [19]

Krambeck et al.

[11] Patent Number: 4,831,205
[45] Date of Patent: May 16, 1989

[54] CATALYTIC CONVERSION OF LIGHT OLEFINIC FEEDSTOCKS IN A FCC PLANT

[75] Inventors: Frederick J. Krambeck, Cherry Hill; Hartley Owen, Belle Mead; Samuel A. Tabak, Wenonah, all of N.J.

[73] Assignee: Mobil Oil Corporation, New York, N.Y.

[21] Appl. No.: 133,825

[22] Filed: Dec. 16, 1987

[51] Int. Cl.$^4$ ............................................... C07C 3/02
[52] U.S. Cl. .................................. 585/519; 585/533
[58] Field of Search ............................. 585/519, 533

[56] References Cited

U.S. PATENT DOCUMENTS 4,090,949  5/1978  Owen et al.
4,471,147  9/1984  Owen et al. ........................ 585/519
4,504,691  3/1985  Hsia et al. .......................... 585/519
4,511,747  4/1985  Wright et al. ................. 585/533 X

FOREIGN PATENT DOCUMENTS 0113180  7/1984  European Pat. Off. .

Primary Examiner—Glenn Caldarola
Attorney, Agent, or Firm—Alexander J. McKillop; Charles J. Speciale; L. G. Wise

[57] ABSTRACT

The separation and recovery of liquid hydrocarbons in a FCC gas plant is removed by integrating therewith an oligomerization reactor which produces liquid hydrocarbons from one of several olefinic streams within the gas plant.

4 Claims, 4 Drawing Sheets

CATALYTIC CONVERSION OF LIGHT OLEFINIC FEEDSTOCKS IN A FCC PLANT

FIELD OF THE INVENTION

This invention relates to the integration of an olefins upgrading process for the catalytic conversion of olefinic feedstocks to liquid hydrocarbons boiling in the gasoline and fuel oil range with the processing and separation of light cracking gases.

BACKGROUND OF THE INVENTION

Hydrocarbon mixtures containing significant quantities of light olefins are frequently encountered in petrochemical plants and petroleum refineries. Because of the ease with which olefins react, these streams serve as feedstocks in a variety of hydrocarbon conversion processes. Many olefinic conversion processes require that the olefinic feed be provided in a highly purified condition. However, processes which may utilize the olefinic feedstocks without the need for further separation and purification are highly desirable.

Although the main purpose of fluidized catalytic cracking (FCC) is to convert gas oils to compounds of lower molecular weight in the gasoline and middle distillate boiling ranges, significant quantities of $C_1$–$C_4$ hydrocarbons are also produced. These light hydrocarbon gases are rich in olefins which heretofore have made them prime candidates for conversion to gasoline blending stocks by means of polymerization and/or alkylation. Fractionation of the effluent from the fluid catalytic cracking reactor has been employed to effect an initial separation of this stream. The gaseous overhead from the main fractionator is collected and processed in the FCC gas plant. Here the gases are compressed, contacted with a naphtha stream, scrubbed, where necessary, with an amine solution to remove sulfur and then fractionated to provide, for example, light olefins and isobutane for alkylation, light olefins for polymerization, n-butane for gasoline blending and propane for LPG. Light gases are recovered for use as fuel.

Since alkylation units were more costly to build and operate than polymerization units, olefin polymerization was initially favored as the route for providing blending stocks. Increased gasoline demand and rising octane requirements soon favored the use of alkylation because it provided gasoline blending stocks at a higher yield and with a higher octane rating than the comparable polymerized product. However, catalytic alkylation can present some safety and disposal problems. In addition, feedstock purification is often required to prevent catalyst contamination. Further, sometimes there is insufficient isobutane available in a refinery to permit all the olefins from the FCC to be catalytically alkylated.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of ZSM-5 or related zeolite. In U.S. Pat. Nos. 4,150,062 and 4,227,992 Garwood et al disclose the operating conditions for the Mobil Olefin to Gasoline Distillate (MOGD) process for selective conversion of $C_3+$ olefins.

The phenomena of shape-selective polymerization are discussed by Garwood in ACS Symposium Series No. 218, Intrazeolite Chemistry, "Conversion of $C_2$–$C_{10}$ to Higher Olefins over Synthetic Zeolite ZSM-5", 1983 American Chemical Society.

In the process for catalytic conversion of olefins to heavier hydrocarbons by catalytic oligomerization using an acid crystalline metallosilicate zeolite, such as ZSM-5 or relate shape-selective catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2$–$C_6$ alkenes may be converted selectively; however, the distillate mode conditions do not convert a major fraction of ethylene due to low severity conditions. While propene, butene-1 and others may be converted to the extent of 50 to 95% in the distillate mode, only about 10 to 50% of the ethylene component will be consumed.

In the high severity or gasoline mode, ethylene and the other lower olefins are catalytically oligomerized at higher temperature and moderate pressure. Under these conditions ethylene conversion rate is greatly increased and lower olefin oligomerization is nearly complete to produce an olefinic gasoline comprising hexene, heptene, octene and other $C_6+$ hydrocarbons in good yield. To avoid excessive temperatures in the exothermic reactors, the lower olefinic feed may be diluted. In the distillate mode operation, olefinic gasoline may be recycled and further oligomerized, as disclosed in U.S. Pat. Nos. 4,211,640 (Garwood and Lee) and 4,433,185 (Tabak). The above cited publications are incorporated herein by reference.

The olefins contained in an FCC gas plant would be an advantageous feed for MOGD as is readily apparent. U.S. Pat. No. 4,090,949 discloses upgrading olefinic gasoline by conversion thereof in the presence of carbon hydrogen-contributing fragments including olefins and a zeolite catalyst and where the contributing olefins may be obtained from a gas plant. U.S. Pat. Nos. 4,471,147 and 4,504,691 disclose an MOGD process using an olefinic feedstock derived from FCC effluent. In these two latter patents the first step involves prefractionating the olefinic feedstock to obtain a gaseous stream rich in ethylene and a liquid stream containing $C_3+$ olefin. While the above patents disclose the general use of olefins obtained from FCC effluent as feedstocks for MOGD conversion, there is not a disclosure of integrating MOGD into gas plant processing so as to improve both the MOGD process and the processing of FCC effluent in a typical FCC gas plant.

Published European Patent Application No. 0,113,180 discloses such integration of MOGD with a FCC plant. In this published application the olefin feedstock for MOGD comprises the discharge stream from the final stage of the wet gas compressor or the overhead from the high pressure receiver which separates the condensed effluent from the final stage wet gas compressor contained in the gas plant. The present invention improves upon such integrated process by incorporating MOGD at different locations in the process stream of the FCC gas plant than the mentioned published European Patent Application.

SUMMARY OF THE INVENTION

This invention relates to an improvement in the process for producing a gasoline fraction and/or a fuel oil fraction by contacting an olefinic feedstock with a shape-selective crystalline aluminosilicate zeolite having a pore diameter greater than 5 Angstrom Units, a silica-to-alumina ratio of at least 12 and a constraint index of from 1 to 12 under reaction conditions effective to convert the olefins to a gasoline fraction and/or a fuel oil fraction, the improvement comprising employing as the feedstock a process stream in the gas plant of a fluid catalytic cracking unit and passing the effluent from the zeolite catalyzed conversion through the separation and recovery facilities of the gas plant to recover the gasoline fraction and/or the fuel oil fraction. Various process streams from the gas plant are contemplated as the feedstock for MOGD conversion. In one embodiment fuel gas ($C_2-$) from the primary absorber ($C_2/C_3$ separator) is converted to gasoline. In a second, maximum conversion of FCC olefins is obtained by converting the discharge stream from the first stage wet gas compressor. In a third alternative, $C_3+$ liquids from the primary absorber are converted under high pressure to distillate fuel.

By utilizing the olefinic feedstreams of a FCC gas plant as feedstocks in the present invention, the need for separate processes for the polymerization or alkylation of the olefins in this stream is obviated or reduced. Also, locating the process of this invention in the FCC gas plant reduces the capital investment and operating costs required for a conversion process of this nature since no new product recovery facilities have to be provided. The effluent from the catalytic conversion can continue through the gas plant which has the facilities required to separate the gasoline fraction and/or fuel oil fraction as blending stocks from the lighter materials.

DETAILED DESCRIPTION OF THE INVENTION

Figure 1:
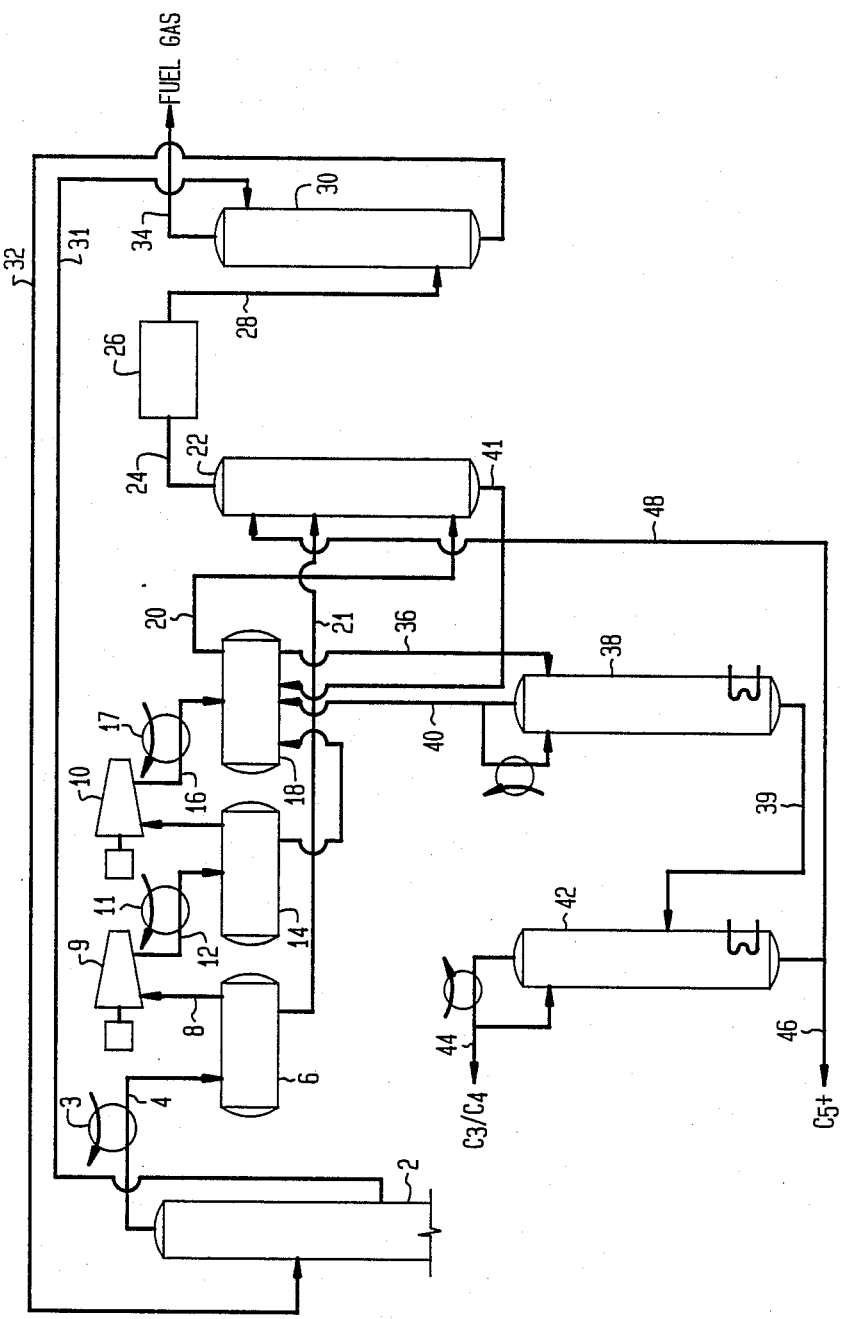
FIG. 1 is a schematic of a typical FCC gas plant.

The present invention contemplates integrating MOGD into a FCC gas plant which is shown in FIG. 1. Referring to FIG. 1, the condensed overhead from the FCC main fractionator 2 flows through indirect heat exchanger 3 via line 4 and into low pressure separator 6 for separation into a gaseous phase and a liquid phase. The gaseous portion from separator 6 flows through line 8 into the suction of first stage wet gas compressor 9 for the initial increase in pressure. The wet gas discharges from first stage compressor 9 through line 12 where the gases are condensed in heat exchanger 11 and discharged into intermediate pressure separator 14. Gases from separator 14 are directed through second stage wet gas compressor 10 from which the effluent is discharged through line 16 where again the gases are condensed in heat exchanger 17 and directed into high pressure separator 18. The purpose of the gas plant is to maximize liquid recovery. Thus, any $C_3$ and $C_4$ hydrocarbons in the gas plant which are recovered as LPG are more valuable than the $C_1$ and $C_2$ fuel gas. Thus, the final high pressure gas from high pressure separator 18 is directed via line 20 to primary absorber 22. In primary absorber 22, $C_5+$ liquids pass in countercurrent flow to the high pressure gas to absorb heavy hydrocarbons including $C_3$ and $C_4$ hydrocarbons from the gas stream. The $C_5+$ liquids employed include the liquid phase from the FCC low pressure separator 6 via line 21 as well as a portion of the final liquid product from the gas plant shown entering absorber 22 via line 48.

The unabsorbed gases pass from the top of absorber 22 through line 24 where the gases may be optionally scrubbed with an ethanol amine scrubber 26 to reduce the acid gases such as sulfur oxides and the like to acceptable levels. The ethanol amine scrubber may be placed prior to absorber 22. The gases pass from line 24 then optionally through scrubber 26 and into line 28 where the gases are directed to sponge absorber 30 where the gases are contacted in countercurrent fashion with sponge oil which is a stripped heavy naphtha or light fuel oil boiling in the 350°–500° F. range. In sponge absorber 30, the $C_3+$ gases are absorbed by the sponge oil which passes from sponge absorber 30 through line 32 into the FCC main fractionating column 2. The unabsorbed $C_2-$ gases pass from absorber 30 through line 34 and are eventually burned as fuel gas.

Regarding the liquid phase in high pressure separator 18, this liquid passes from the receiver through line 36 to stripper 38 where steam is employed to remove the light gases from this stream. The steam and light gases pass from the top of stripper 38 through line 40 and discharge back into high pressure separator 18 from which the useful light gases are recovered.

The stripped $C_3+$ liquid passes from stripper 38 through line 39 to debutanizer 42 where a $C_4-$ fraction is separated and passes from the column as overhead through line 44 where it is recovered as LPG product. Gasoline and/or fuel oil fraction ($C_5+$) is removed from debutanizer 42 as the bottoms fraction through line 46. A portion of this fraction is recycled through line 48 to primary absorber 22 as a portion of the absorbing liquid as described previously. The remaining portion of the $C_5+$ bottoms is recovered as product and can be employed as blending stock for gasoline and/or fuel oil following further fractionation as required.

In the present invention it is the above-described gas plant which has integrated therewith the MOGD conversion reactor. The oligomerization catalyst preferred for use in MOGD include the medium pore (i.e., about 5-7 angstroms) shape selective crystalline aluminosilicate zeolites having a silica to alumina ratio of at least 12, a constraint index of about 1-12 and acid cracking activity of about 50-200. Representative of the shape selective zeolites are ZSM-5, ZSM-11, ZSM-12, ZSM-22, ZSM-23, ZSM-35, ZSM-38, and ZSM-48. ZSM-5 is disclosed in U.S. Pat. No. 3,702,886 and U.S. Pat. No. Reissue 29,948. Other suitable zeolites are disclosed in U.S. Pat. Nos. 3,709,979 (ZSM-11); 3,832,449 (ZSM-12); 4,076,979; 4,076,842 (ZSM-23); 4,016,245 (ZSM-35); 4,046,339 (ZSM-38); and 4,375,573 (ZSM-48). The disclosures of these patents are incorporated herein by reference.

A further useful catalyst is a medium pore shape selective crystalline aluminosilicate zeolite as described above containing at least one Group VIII metal, for example Ni-ZSM-5. This catalyst has been shown to convert ethylene at moderate temperatures and is disclosed in a copending U.S. patent application Ser. No. 775,906, filed Sept. 13, 1985.

The catalyst for oligomerization of the olefinic feed can be composited with a suitable binder such as alumina and shaped in the form of cylindrical extrudates of about 1-5 millimeters diameter for use in fixed bed operation or particle size for use in fluid bed operation. Other pentasil catalysts which may be employed for converting lower olefins include a variety of medium pore (5 to 9A) siliceous materials such as borosilicates, ferrosilicates, and/or aluminosilicates disclosed in U.S. Pat. Nos. 4,414,423; 4,417,086; and 4,517,396, incorporated herein by reference.

The general operating parameters for MOGD in the process of the present invention can be defined by stating that the process is carried out at pressures from about 100-1000 psig, at temperatures ranging from about 350°-700° F., and at a space velocities of 0.2-10 LHSV. It is to be immediately understood that the above recitation of ranges of pressure, space velocity, and temperature is not intended to mean that all operations within the above set forth limits will result in producing the desired results of the invention. On the contrary, what is meant by the above limits concerning temperature, pressure, and space velocity is best expressed in a negative way. In other words operations outside the ranges specifically set forth will not result in the improved process of this invention. It is well known in the art that there is a correlation between temperature, pressure, and space velocity with respect to the severity of a given chemical reaction. Quite simply put, the instant invention is concerned with the first stage oligomerization of a light olefinic stream to gasoline and distillate fuel range products.

To operate the MOGD to obtain a greater proportion of distillate fuels, the reaction is run at moderate temperature of 375°-600° F. and relatively high pressure of about 600-1000 psig. On the other hand, for producing a greater proportion of gasoline, the operation is run at elevated temperature 450°-700° F. and more moderate pressure of about 50-400 psig. The MOGD reactor can be fixed, moving or fluidized bed.

Figure 2:
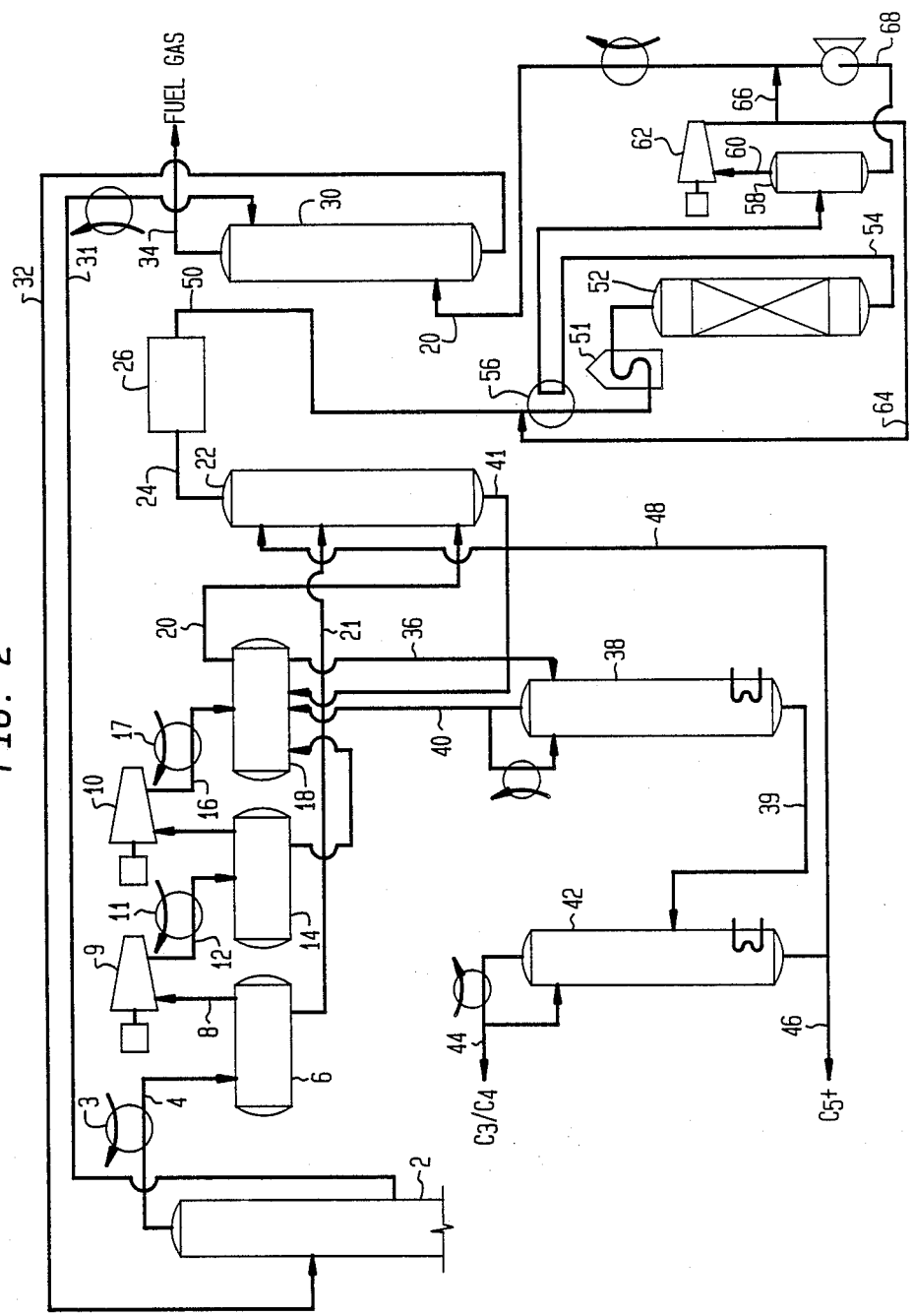
FIG. 2 is a schematic of a typical FCC gas plant with MOGD for fuel gas conversion.

Referring now to FIG. 2, an MOGD reactor is integrated into the FCC gas plant so as to convert the fuel gas, i.e., $C_2$—, to liquid hydrocarbons. Thus, the fuel gas-containing stream leaving primary absorber 22 or acid gas scrubber 26 is now routed into a low pressure MOGD reactor instead of directly into sponge absorber 30. The fuel gas stream leaves acid gas scrubber 26 via line 50 and is directed to the top of MOGD reactor 52 via line 51 after heating to conversion temperature in indirect heat exchanger 53 and furnace 55. The fuel gas stream entering MOGD reactor 52 comprises typically at least about 20 wt. % $C_2$— hydrocarbons and, preferably will contain about 50 wt. % of such fuel gas.

The MOGD reactor is run under low pressure and high temperature, conditions sufficient to convert the $C_2$ olefin into gasoline range hydrocarbons. As stated above it is difficult to convert ethylene into distillate range fuels at high pressure and moderate temperature as only a relatively small portion of the ethylene is converted. Thus, in the embodiment illustrated in FIG. 2 the MOGD reactor is run at a low pressure, typically about 800 to 2200 kPa (100 to 360 psig) which equals the gas plant pressure or slightly below same and temperatures above about 500° F. The effluent exits the bottom of MOGD reactor 52 via line 54 where it is condensed in heat exchanger 56 by heating the incoming fuel gas feed. The condensed effluent is passed to high pressure separator 58. The gas leaving separator 58 via line 60 is compressed in compressor 62. A portion of the compressed gas is recycled via line 64 for cooling the MOGD liquids in heat exchanger 56. The remainder of the gas is blended via line 66 with liquid leaving high pressure separator 58 via line 68 and the mixed stream is directed to sponge absorber 30 via line 70. In sponge absorber 30, the liquid will be sponged up and returned to the main FCC distillation column 2 as discussed with respect to FIG. 1.

Figure 3:
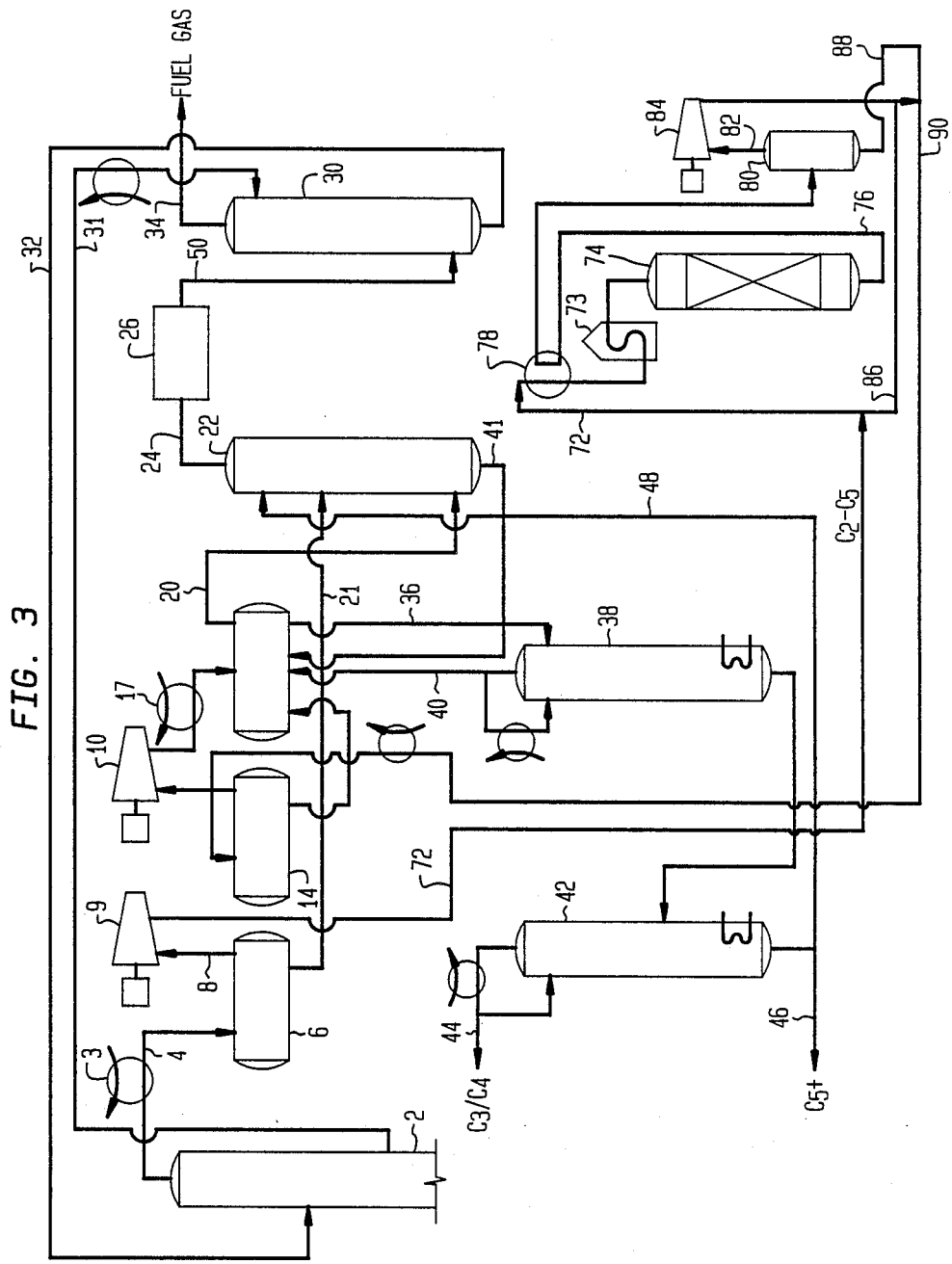
FIG. 3 is a schematic of a typical FCC gas plant with MOGD for fuel gas and $C_3+$ conversion.

An alternative for integrating MOGD into an FCC gas plant is shown in FIG. 3. In this alternative, the MOGD reactor is incorporated into the FCC gas plant for maximum conversion of FCC olefins. In this process, the total gas stream coming off compressor 9 via line 12 is directed via line 72 to heat exchanger 78 and furnace 73 for heating to conversion temperature prior to entering MOGD reactor 74, thereby temporarily bypassing intermediate pressure separator 14. The stream which enters MOGD reactor 74 is rich in all of the FCC oleins. A typical composition of this stream is given in Table 1.

TABLE 1

COMPOSITION OF DISCHARGE FROM FIRST STAGE COMPRESSION

| Component | Volume % |
|---|---|
| $O_2$ | 0.1 |
| $N_2$ | 3.24 |
| $H_2O$ | 2.28 |
| $CO_2$ | 0.67 |
| $H_2S$ | 6.21 |
| $H_2$ | 3.42 |
| C1 | 16.49 |
| $C_2=$ | 6.99 |
| C2 | 7.33 |
| $C_3=$ | 16.02 |
| C3 | 6.05 |
| iC4 | 5.83 |
| nC4 | 1.73 |
| $C_4=$ | 13.19 |
| iC5 | 2.77 |
| nC5 | 0.29 |
| $C_5=$ | 5.34 |
| C6+ | 2.05 |

Conditions in the MOGD reactor can vary within the limits previously described to form liquid hydrocarbon but most preferably will be such so as to produce a gasoline range hydrocarbon liquid which leaves MOGD reactor 74 via line 76. The liquid is condensed in heat exchanger 78 and heats the feed entering reactor 74 via line 72 and then is passed through high pressure separator 80. Gas leaving separator 80 via line 82 is compressed in compressor 84. A portion of this gas can be recycled to the feed via line 86. The liquid which has dropped out of separator 80 via line 88 and gas from compressor 84 which is not recycled are combined and directed to intermediate pressure separator 14 via line 90 where the normal FCC gas plant separation process continues as discussed with respect to FIG. 1.

In the process as depicted in FIG. 3, maximum conversion of olefins from FCC conversion is obtained. Moreover, integrating MOGD into the FCC gas plant off the first compressor bebottlenecks the FCC gas plant. Thus, by converting the propylene, butylene, and ethylene to gasoline at this stage in the gas plant, the amount of gas which enters the second stage compressor 10 is substantially reduced. Additionally, the amount of gas which enters primary absorber 20 and sponge absorber 30 as well as stripper 38 is substantially reduced since much of what is directed to MOGD reactor 74 will drop out of separator 14 as gasoline. This gasoline can be stripped very easily and go out through the bottom of debutanizer 42. Thus, the throughput to primary absorber 22, sponge absorber 30 and the duty on stripper 38 is greatly reduced. This alternative also allows reduced horse power requirement in the second stage compressor 10. Using this alternative, the gas plant size of FCC can be reduced or the throughput through existing FCC gas plant can be increased.

Figure 4:
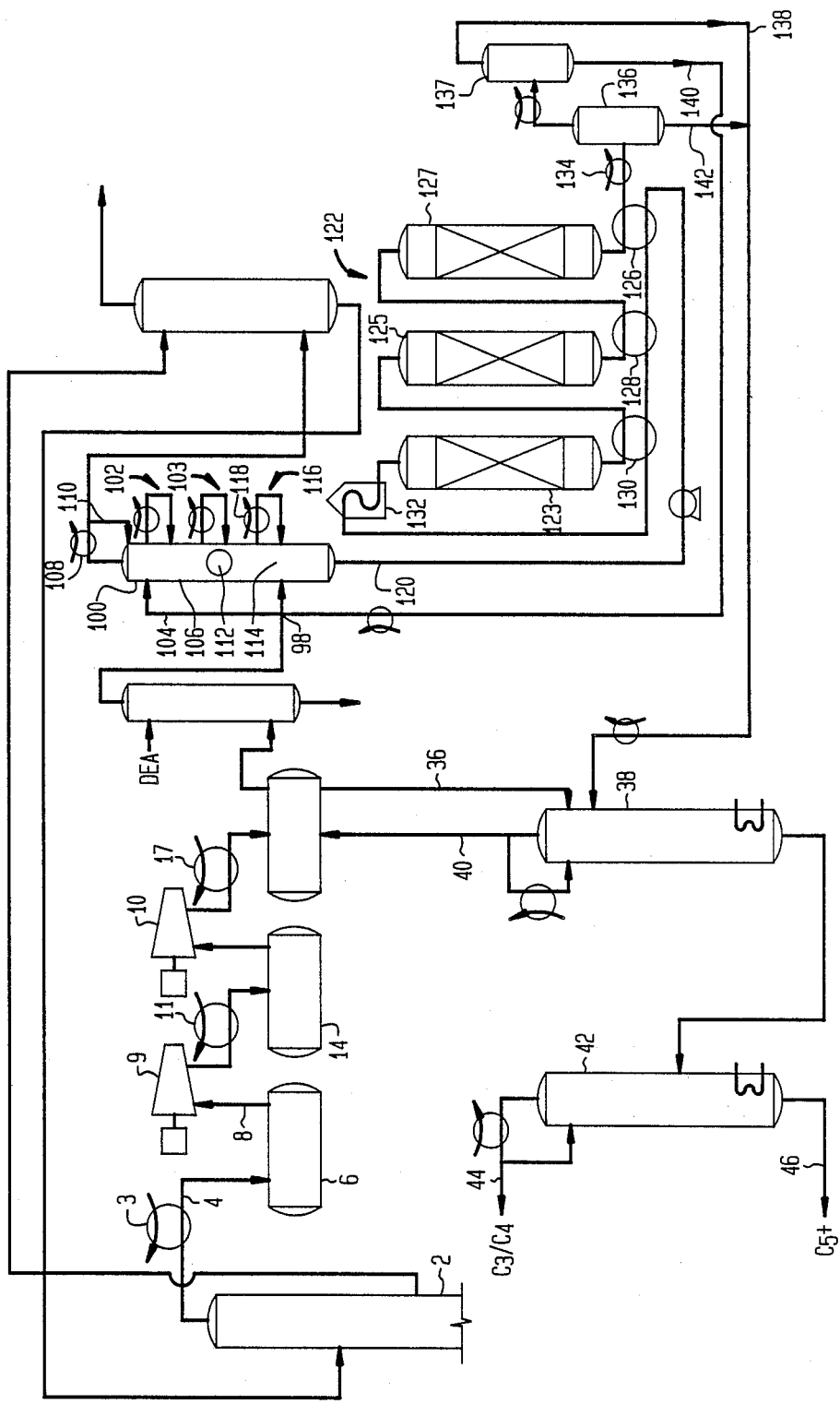
FIG. 4 is a schematic of a typical FCC gas plant with MOGD for $C_3+$ conversion.

FIG. 4 illustrates an alternative integration of MOGD into an FCC gas plant yy utilizing the primary absorber 22 to sorb $C_3+$ materials and for pumping these materials up to MOGD operating pressure. As shown in FIG. 4, gas from high pressure separator is directed to the primary absorber 100, (optionally after acid gas scrubbing) via line 98.

Sorption tower 100, as depicted, has multiple contact zones, with the heat of absorption being removed via interstage pump around cooling means 102, 103. The liquid gasoline sorbent is introduced to the sorption tower through line 104 above the top contact section 106. It is preferred to mix incoming liquid sorbent with recycled splitter overhead which is condensed in condenser 108 and enters absorber 100 via line 110. Liquid sorbent from line 104 and recycle stream 110 is then pumped to the upper portion of absorber 100 for countercurrent contact in a plate column or the like with upwardly flowing ethylene rich vapors. Liquid from the bottom of upper contact zone 106 is pumped to a heat exchanger in loop 102, cooled and returned to the tower above intermediate contact zone 112, again cooled in loop 103, and returned to the tower above contact zone 114, which is located below the feedstock inlet via line 98. Under tower design conditions of about 2100 kPa (300 psia), it is preferred to maintain liquid temperature of streams entering the tower from 102, 103 and 110 at about 40° C. (100° F.). The lower contact zone 114 provides further fractionation of the olefin-rich liquid.

The liquid sorbate-sorbent mixture is withdrawn through bottom outlet 120 and pumped to reaction in MOGD reactor system 122.

The MOGD reactor system 122 shown consists of three downflow fixed bed, series reactors on line with exchanger cooling between reactors. The reactor configuration allows for any reactor to be in any position, 123, 125, or 127. The reactor in position 123 has the most aged catalyst and the reactor in position 127 has freshly regenerated catalyst.

The $C_3+$ feedstream leaving absorber 100 via line 120 is pressurized by pump 124 and then sequentially heated by passing through indirect heat exchange units 126, 128, 130 and furnace 132 to achieve the temperature for catalytic conversion in MOGD reactor system 12, including plural reactor vessels 123, 125 and 127. MOGD conversion conditions are preferably such as to produce a distillate range liquid hydrocarbon. Thus, high pressure, about 4225 kPa to 14000 kPa (600 to 2000 psig), and relatively low temperatures of about 200° to 345° C. (400° to 650° F.) are maintained.

The reactor effluent is cooled by indirect heat exchange in condenser 134. The condensed effluent is separated by the high temperature separator 136 and low temperature separator 137 into light 138, intermediate 140 and heavy 142 range hydrocarbons. Heavy range hydrocarbons via line 142 and light range hydrocarbon via line 138 are directed to the gasoline stripper 38 along with liquid from separator 18. Intermediate range hydrocarbons via line 140 are used as the gasoline sorbent and enters absorber 100 via line 104. The normal operation of the gas plant then continues as discussed with respect to FIG. 1.

What is claimed is:
1. In a process for separating and recovering liquid hydrocarbons from a distillation overhead stream from a distillation column which separates effluent from fluidized catalytic cracking conversion, said overhead stream comprising at least 10 mole % $C_1$-$C_4$ olefin-containing gases, wherein said overhead stream is partially condensed and separated into a first gaseous phase and a first liquid phase in a low pressure separator, said first gaseous phase is compressed in a first stage wet compressor, said compressed first gaseous phase is further condensed and separated into a second gaseous phase and second liquid phase in an intermediate pressure separator, at least a portion of said second gas phase from said intermediate pressure separator is compressed in a second stage wet gas compressor, said compressed gaseous phase from said second stage wet gas compressor is further condensed and separated into a gaseous and liquid phase in a high pressure separator, said gaseous phase from said high pressure separator is scrubbed with a $C_5+$ hydrocarbon liquid in an absorber to absorb $C_3+$ hydrocarbons from said scrubbed gaseous phase and form a gaseous nonabsorbed effluent rich in $C_2-$ fuel gas, including ethylene, and said rich fuel gas effluent is scrubbed with a distillate range liquid hydrocarbon sponge oil to remove $C_3+$ hydrocarbons from said rich fuel gas effluent, the improvement comprising;
contacting said second gaseous phase recovered from said first stage wet compressor in an oligomerization reactor with a medium pore zeolite catalyst under conditions such as to oligomerize said olefins to a product comprising gasoline or distillate fuel range hydrocarbons, and wherein total effluent from said oligomerization reactor is sequentially cooled and directed to said intermediate pressure separator, whereby substantially all $C_6+$ oligomerization components are separated and recovered as a liquid product stream.

2. The process of claim 1 wherein said fuel gas comprises at least 5 mole % ethylene.

3. A process for upgrading olefinic hydrocarbons from a light olefinic hydrocarbon distillation overhead stream from a distillation column which separates catalytic cracking byproducts, said overhead stream comprising at least 10 mole % $C_1$-$C_4$ olefinic light hydrocarbon gases, comprising the steps of:
partially condensing and separating said overhead stream into a first gaseous phase and a frrst liquid phase in a low pressure separator;
compressing said first gaseous phase in a first stage wet gas compressor;
contacting said compressed first gaseous phase recovered from said first stage compressor in an oligomerization reactor with a medium pore shape selective acid zeolite catalyst at elevated temperature under conditions to convert at least a portion of said olefins to a product comprising $C_6+$ hydrocarbons;
cooling total effluent from said oligomerization reactor and directing partially condensed reactor effuuent to an intermediate pressure separator, whereby substantially all $C_6+$ oligomerization components are separated and recovered as a liquid stream;
further compressing a gaseous portion of said reactor efluent from said intermediate pressure separator in a second stage wet gas compressor, said compressed gaseous phase from said second stage wet gas compressor being further condensed and separated into a gaseous and liquid phase in a high pressure separator;

contacting high pressure gas from said high pressure separator with a $C_5+$ hydrocarbon liquid in an absorber to absorb $C_3+$ hydrocarbons from said high pressure gas to provide a nonabsorbed light gas effluent rich in $C_2-$ gas; and recovering $C_5+$ hydrocarbon liquid from absorber liquid to provide a gasoline or distillate product stream and a liquid absorber recycle stream.

4. The process of claim 3 wherein said first liquid phase from said low pressure separator is sent directly to said absorber.

* * * * *